US012514719B2

(12) United States Patent
Guercini et al.

(10) Patent No.: US 12,514,719 B2
(45) Date of Patent: Jan. 6, 2026

(54) ROBOTIC ANKLE

(71) Applicants: FONDAZIONE ISTITUTO ITALIANO DI TECNOLOGIA, Genoa (IT); I.N.A.I.L.—ISTITUTO NAZIONALE PER L'ASSICURAZIONE CONTRO GLI INFORTUNI SUL LAVORO, Rome (IT)

(72) Inventors: Lorenzo Guercini, Rome (IT); Simone Traverso, Genoa (IT); Matteo Laffranchi, Genoa (IT); Lorenzo De Michieli, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 532 days.

(21) Appl. No.: 18/248,546

(22) PCT Filed: Nov. 9, 2021

(86) PCT No.: PCT/IB2021/060354
§ 371 (c)(1),
(2) Date: Apr. 11, 2023

(87) PCT Pub. No.: WO2022/101775
PCT Pub. Date: May 19, 2022

(65) Prior Publication Data

US 2023/0372125 A1 Nov. 23, 2023

(30) Foreign Application Priority Data

Nov. 12, 2020 (IT) ........................ 102020000027104

(51) Int. Cl.
*A61F 2/66* (2006.01)
*A61F 2/50* (2006.01)
(Continued)

(52) U.S. Cl.
CPC ............ *A61F 2/6607* (2013.01); *A61F 2/741* (2021.08); *A61F 2002/5006* (2013.01); *A61F 2002/701* (2013.01)

(58) Field of Classification Search
CPC .................... A61F 2/6607; A61F 2/741; A61F 2002/5006; A61F 2002/701; A61F 2002/5003
See application file for complete search history.

(56) References Cited

U.S. PATENT DOCUMENTS 11,278,235 B2 * 3/2022 Herr ....................... A61B 5/688
2015/0209159 A1 * 7/2015 Goldfarb .................. A61F 2/66
73/862.541

(Continued)

FOREIGN PATENT DOCUMENTS

CN 111200996 A 5/2020
EP 3248576 A2 11/2017

OTHER PUBLICATIONS

International Search Report and Written Opinion for Corresponding International Application No. PCT/IB2021/060354, Dec. 22, 2021, 9 pages.

*Primary Examiner* — Nitin Patel
(74) *Attorney, Agent, or Firm* — LUCAS & MERCANTI, LLP

(57) ABSTRACT

An ankle prosthesis is disclosed having an actuation system so as to act as a brake, modulated by motor means, proportional to the load stressing the prosthesis. The prosthesis is advantageously capable of reducing the work necessary to lift the prosthesis while maintaining an anthropometric encumbrance.

14 Claims, 2 Drawing Sheets

(51) Int. Cl.
*A61F 2/70* (2006.01)
*A61F 2/74* (2006.01)

(56) References Cited

U.S. PATENT DOCUMENTS

| | | | | |
|---|---|---|---|---|
| 2018/0085237 | A1* | 3/2018 | Gao | A61F 2/6607 |
| 2019/0231562 | A1* | 8/2019 | Pusch | A61F 5/0102 |
| 2020/0129314 | A1 | 4/2020 | Herr et al. | |
| 2020/0188138 | A1* | 6/2020 | Arelekatti | A61F 2/644 |
| 2021/0298925 | A1* | 9/2021 | Dehez | A61F 2/68 |
| 2022/0062009 | A1* | 3/2022 | Lecomte | A61F 2/70 |
| 2022/0160522 | A1* | 5/2022 | Herr | A61F 2/6607 |
| 2023/0329885 | A1* | 10/2023 | Lipsey | A61F 2/6607 |
| 2025/0302644 | A1* | 10/2025 | Haque | A61F 2/6607 |

* cited by examiner

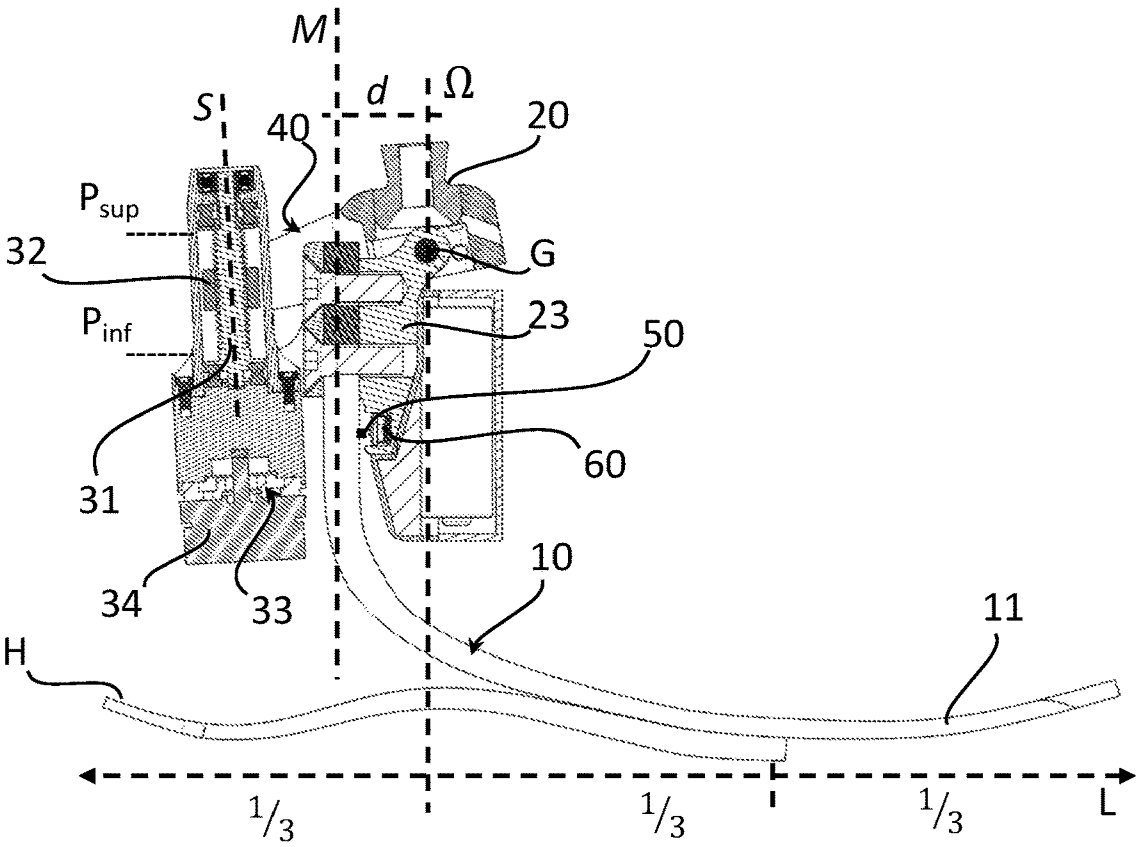
Fig. 3
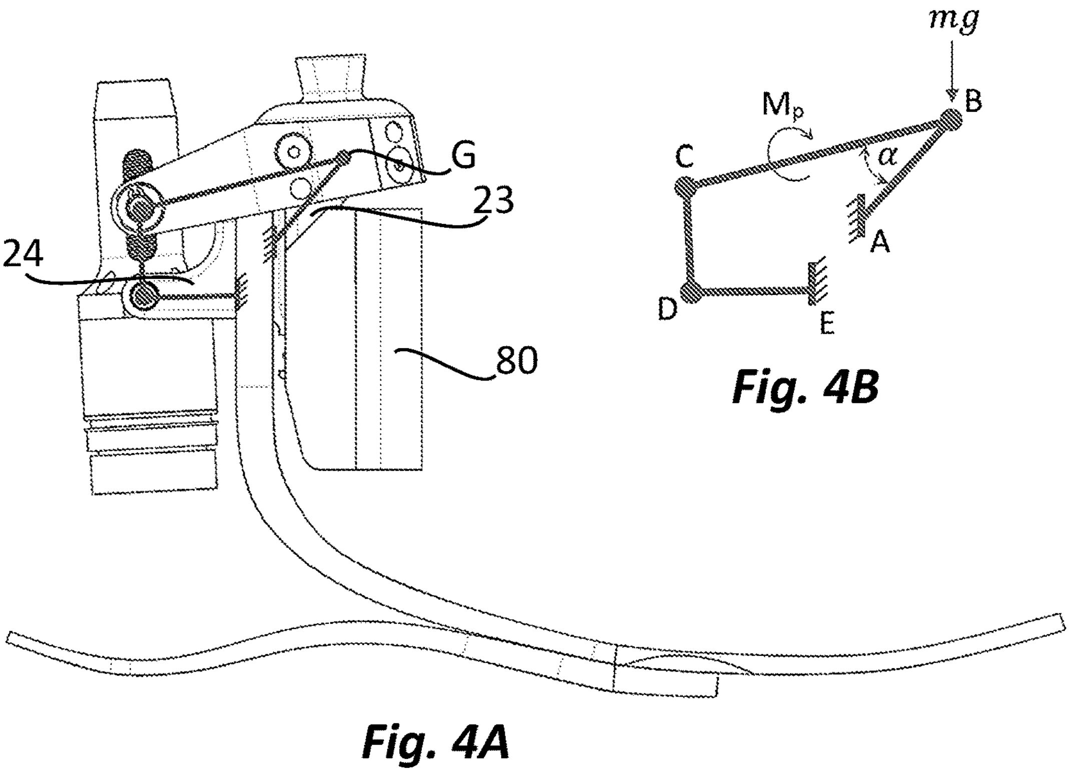
Fig. 4B
Fig. 4A

ROBOTIC ANKLE

CROSS-REFERENCE TO RELATED APPLICATIONS

This application is a 371 of PCT/IB2021/060354, filed Nov. 9, 2021, which claims the benefit of priority from Italian Patent Application No. 102020000027104, filed Nov. 12, 2021.

TECHNICAL FIELD OF THE INVENTION

The present invention relates to the field of the prosthetic devices, in particular of robotic type.

More specifically, the invention provides an orthopaedic exoprosthesis to replace the ankle joint, with improved features of effectiveness and compactness.

BACKGROUND

Amputation causes can be of various nature, for example congenital/pathological or even accidental in case of accidents or injuries.

In order to face the obvious discomforts involved by an amputation, the use of prosthetic devices is known, which allow to replace (partially or wholly) a skeletal segment with the purpose of restoring as much as possible both aesthetics and the function of the missing body portion.

Exoprostheses, for example, are devices wholly applied outside the body of the amputated subject and, typically, they are applied to the residual limb stumps through different construction solutions.

At the level of the lower limbs, and depending upon the amputation point, different types of exoprostheses are available. In case of a transtibial amputation, such devices compensate the loss of the foot and tibia's portion, while maintaining unaltered the knee functionality.

Generally, the transtibial prostheses provide a supporting element, for example in form of a storage, to receive the limb stump (or additional prosthetic devices), a series of components which cooperate to each other so as to replicate the ankle joint, and a contact element (or artificial foot) on the walking surface.

The so-called "active" prostheses are energy-intensive systems which further comprise actuation means configured to provide an active control of the motion of the prosthesis itself, as user's walking aid.

In some cases, said actuation means contributes to lift (toe clearance) the prosthesis with respect to the walking surface, to reduce the stumbling risk during the foot's swinging phase (swing). In other cases, they provide for dissipating the energy due to the impact during the resting phase (stance) of the prosthesis and to the torques generated by the ankle joint, to limit the patient's pain to his/her stump.

However, the known solutions are improvable systems. None of them allows to integrate, in the same device, an actuation system acting both to dampen the step during the walking stance phase and to generate toe clearance in the swing phase, while maintaining an anthropometric ankle encumbrance.

Typically, the prosthetic ankles dissipating energy avail of micro-controlled dampers and they do not provide active actuation means to provide toe clearance. For example, CN111200996A discloses a damping device wherein the damping effect by mechanical friction is generated by the friction between the piston surface and the internal wall of a cylinder. Vice versa, the known prosthetic ankles favouring the foot lifting generally avail of not back-drivable mechanical elements which then are not capable of absorbing energy during the stance phase.

The known prosthetic ankles trying to combine both above-described operating conditions generally use extremely effective kinematic chains (with performances higher than 80%), however requiring powerful motor means (even above 100 W) which make them expensive, heavy, bulky and having reduced energy reduction.

For example, US 2020/129314 A1 discloses an ankle prosthesis wherein the damping system results to be integrated in the stump supporting element and EP 3248576 A2 discloses a prosthetic ankle wherein the actuation is implemented through a hydraulic system of piston-cylinder type.

BRIEF DESCRIPTION OF THE INVENTION

The technical problem placed and solved by the present invention is then to overcome one or more of the above-illustrated problems and, in particular, to provide an ankle prosthesis with an anthropometric encumbrance structure configured both to absorb kinetic energy in the stance phase and to provide an aid to the lifting from the walking surface during the swing phase. This is obtained by an ankle prosthesis as defined in claim 1.

Additional features of the present invention are set forth in the corresponding depending claims.

The concept underlying the present invention is to provide an ankle prosthesis implementing an actuation system so as to act as brake, modulated by motor means, proportional to the load stressing the prosthesis (for example an axial load in the stance phase), which system is advantageously capable of reducing the work required for lifting (toe clearance) the prosthesis itself, while maintaining an anthropometric encumbrance.

In a preferred embodiment, the ankle prosthesis of the invention comprises a main body equipped with a foot portion configured to rest on a walking surface, and stump supporting means configured to couple with a leg element.

The prosthesis comprises linear actuation means, comprising a coupling having a friction coefficient lower than 0.16 between a screw element and a nut screw element. The actuation means is movable between an advanced position and a rearward position.

The stump supporting means, the screw element and the nut screw element are constrained to the main body according to a substantially four-bar linkage configuration, so that a relative rotation between the supporting means and the main body is allowed.

The configuration of the prosthesis is so that during a resting phase the foot portion comprises at least a first and a second contact position on the walking surface. A respective opposite motion of the actuation means between said advanced position and said rearward position corresponds to said first and second contact position, preferably subsequent to each other, during a damping condition of the loads transferred on said main body by the leg element.

The precise selection of such architecture allows to obtain a transmission efficiency of the screw-nut screw coupling preferably equal to about 50%. In other words, the four-bar linkage configuration allows the actuation means to act as damping element in their bidirectional motion along a direction, thereto one will refer in the present description as damping direction, which is preferably parallel, or coincides, with the axis of the screw element.

In this sense, when the prosthesis of the invention is subjected to a load, for example in the above-mentioned resting phase, the nut screw acts as a proportional brake with respect to the load which has to sustain, by offering a resistant torque which can prevent a backward motion thereof. The above-mentioned coupling is actuated by motor means which then have to provide contained engine torque values in the direction of the applied load, to obtain a relative motion of the supporting element with respect to the main body. In other words, the actuation of the screw element is favoured since the stress transferred on the prosthesis results to be annulled, or annullable, by the resistant torque offered by the nut screw.

This means for example that, for a high input torque at the user's ankle, for example generated by the progression during walking, the motor means perceives a torque lower than 0.05% of the input torque, to the benefit of the possibility of reducing the required power to be made available with the motor means, their consumption and encumbrance under condition assembled on the prosthesis.

It is to be noted that the absorption of very high torques through the use of under-sized actuating means (that is with an active power lower than 20% with respect to the power to be dissipated), while maintaining the capability of actuating the joint when the latter is not under load, generally is a very common problem in prosthetic robotics and not only. The inventive concept underlying the present invention, even if applied to an ankle prosthesis, then can even be implemented in different types of prostheses (for example knee prostheses) or exoskeletons.

The above-mentioned friction coefficient is preferably obtained starting from selected treatments of the screw-nut screw coupling, for example through diamond like carbon (DLC) coating applied to the screw element. In this way the system efficiency is improved without sacrificing a high transmission ratio. Analogous treatments advantageously allow to make the nut screw of steel instead of bronze (as it is known in the couplings of this type) by increasing the yield strength of the component and thus implementing a more compact mechanism.

Advantageously, in preferred embodiments and in combination with a selected type of adopted treatment, the prosthesis of the invention provides the use of a screw element having a thread which has a helix angle comprised between specific values, preferably between 3° and 11°. Such helix angle values of the screw determine a coupling efficiency allowing to reduce to a minimum the sizes of the motor means and the energy consumption thereof, by following the above-mentioned concept of proportional brake.

Still, the prosthesis preferably comprises sensor means configured to adjust the motion of the actuation means depending upon the detection of a bending of said main body, for example by detecting a user's unbalance in a prodromal phase upon executing a step.

The prosthesis then can return a behaviour compliant to the user's needs, by adapting to the type of ground or walk, reducing the shocks to the user's stump and moving actively to ease walking by providing the correct behaviour during the various walking phases.

Other advantages, together with the features and use modes of the present invention, will result evident from the following detailed description of preferred embodiments thereof, shown by way of example and not for limitative purposes.

BRIEF DESCRIPTION OF FIGURES

The drawings shown in the enclosed figures will be referred to, wherein:

FIG. 3 shows a section view of the ankle prosthesis as illustrated in FIG. 2;

FIGS. 4A and 4B show the ankle prosthesis as illustrated in FIG. 2 associated to a graph model representing the kinematics of its components and the kinematic model itself, respectively.

DETAILED DESCRIPTION OF EMBODIMENTS OF THE INVENTION

The present invention will be described hereinafter by making reference to the above-mentioned Figures.

Figure 1:
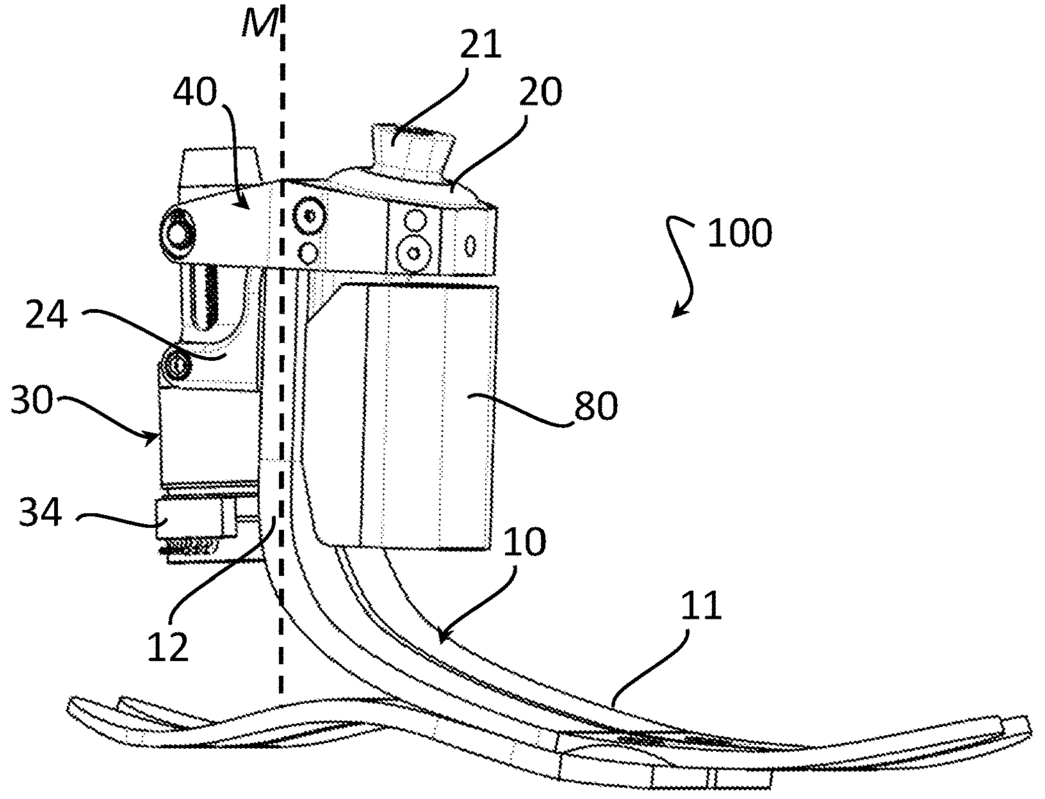
FIG. 1 shows an overall view of a preferred embodiment of an ankle prosthesis according to the present invention.
Figure 2:
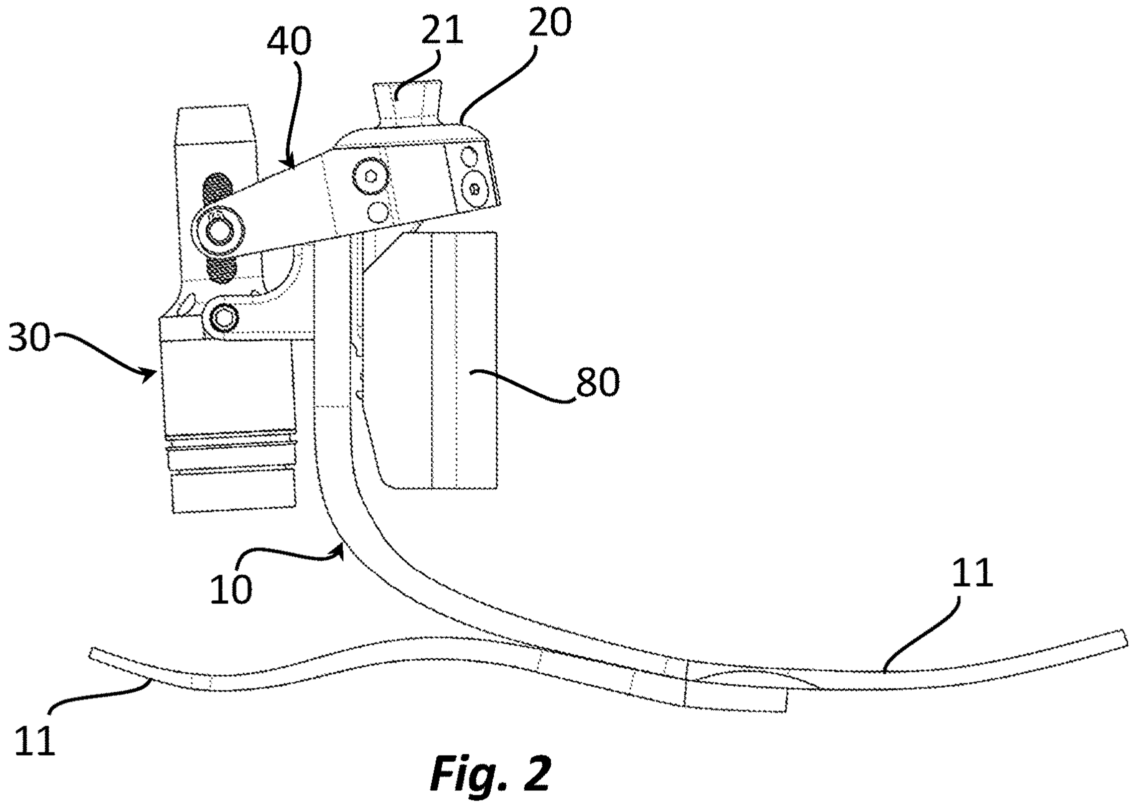
FIG. 2 shows a side view of the ankle prosthesis of FIG. 1.

By firstly referring to FIG. 1 a preferred embodiment of an ankle prosthesis 100 according to the present invention is shown.

The ankle prosthesis 100 is an active prosthesis, having reduced weight and high efficiency, which can be used independently from the transtibial amputees or, in combination with other prosthetic devices, from subjects showing a higher amputation level.

As it can be seen, the prosthesis 100 comprises a main body 10 equipped with a foot portion 11 configured to rest on a walking surface.

The main body 10 is made of flexible material and comprises an upright element 12 joined to the foot portion 11. The upright element 12 is preferably shaped so as to extend according to a direction M substantially orthogonal with respect to the plane comprising the foot portion 11.

In a preferred embodiment of the invention, exemplified in the present description, the upright element 12 and the foot portion 11 define a foot structure, preferably made of carbon fibre, to return energy.

The upright element 12 allows to sustain means for supporting a stump (of a limb or other prosthetic device) designated with reference 20, linear actuation means designated as a whole with reference 30, and preferably additional components of the prosthesis 100 which will be described later.

The supporting means 20 is configured to couple with a leg element and comprises an attachment 21, preferably of pyramidal type, known for the person skilled in the art and thereupon one will not dwell hereinafter.

By further referring to FIG. 3, the supporting means 20 is assembled rotatably, for example through bushing bearings, on a (pivot) shaft constrained to the main body 10 at a joint G. The joint G detects the main rotation centre of the ankle prosthesis 100.

Preferably, said pivot is constrained to the main body 10 through a first stirrup 23 fastened to the upright element 12 and so that the joint G results to be positioned at a distance d with respect to the extension direction M of the upright element 12.

In a preferred embodiment, the joint G lies on an axis Ω, parallel to said direction M, and which orthogonally intercepts a direction of longitudinal development L of the foot portion 11—when resting on the walking surface—at one third of its extension with respect to a heel terminal end H.

The linear actuation means 30 comprises motor means 34 operatively connected to a screw element 31 coupled to a nut screw element 32. Advantageously, said coupling has a friction coefficient lower than 0.16. The actuation means 30 is constrained to said main body 10, preferably through a second stirrup 24 which connects them to the upright element 12. The motor means 34 can include for example a brushless direct current (BLDC) motor.

In an embodiment, the actuation means 30 further comprises a reduction stage, preferably a planetary reduction gear 33, interposed between the screw element 31 and the motor means 34. The planetary reduction gear 33 allows the motor means 34 a better management of the torque fluctuations given by the friction instability of the coupling between the screw element 31 and the nut screw element 32.

The supporting means 20, said screw element 31 and said nut screw element 32 are constrained to the main body 20 according to a substantially four-bar linkage configuration 40 so as to allow a relative rotation between said supporting means 20 and said main body 10.

The above-mentioned four-bar linkage configuration 40 is so as to further allow a bi-directional motion of the actuation means 30 between an advanced position $P_{sup}$ and a rearward position $P_{inf}$.

In a resting phase of the prosthesis 100 on the walking surface, a damping condition of the loads transferred on the main body 10 by the leg element corresponds to a motion of the actuation means 30 between the backward position $P_{inf}$ and the advanced position $P_{sup}$.

The four-bar linkage configuration 40 then allows the actuation means 30 to act as damping element along a damping direction S which, preferably, is parallel, or coincides, to the axis of the screw element 31. Said advanced position $P_{sup}$ and said rearward position $P_{inf}$ are detected by the actuation means 30 in their own motion along said damping direction S.

Advantageously, the four-bar linkage configuration 40 is so that the main body 10 is interposed between the joint G and the actuation means 30. Preferably, the joint G protrudes frontally from the upright element 12 and with respect to an advancing direction of the prosthesis 100, whereas the actuation means 30 is positioned as a whole on the rear side of the upright element 12. Such arrangement allows to improve the stability conferred by the prosthesis 100 during walking and to increase the energy return produced by the flexible body 10.

By further referring to FIGS. 4A and 4B, the four-bar linkage configuration 40 preferably comprises a first arm DC and a second arm BC.

Said first arm DC has a variable extension depending upon the rotation of the supporting element 20. In particular, such extension results to be variable between the above-mentioned advanced position $P_{sup}$ and the backward position $P_{inf}$.

In particular, FIG. 4B shows a scheme of the connections implementing the four-bar linkage configuration 40 and the kinematics of the four-bar linkage 40 implemented in the embodiment of the prosthesis 100 of the invention is described hereinafter.

The element AB and the element DE are static elements since they include a fixed end, integral to the main body 10, in particular to the upright element 12.

Under a starting resting condition, or stillness condition, the user of the prosthesis 100 is standing and motionless, with the foot portion 11 rested on the walking surface. Under such initial condition, the load transferred by the leg element is exemplified with the weight force (designated with reference mg in FIG. 4B) and it crosses the main rotation centre (designated with 8) of the prosthesis 100 which, as said, corresponds to the joint G.

Under such initial resting condition, the static element AB of the four-bar linkage 40 transmits said weight force to the main body 10. No torsional moment is generated by the user.

When the user unbalances the load, for example during the step cycle (by referring to the above-mentioned initial resting condition) moving its mass centre with respect to the rotation axis 8, a torque is generated on said second arm BC.

During the step cycle and in general terms, that is, a resting phase of the main body 10 comprises a plurality of contact conditions, typically partial contact, of the foot portion 11 on the walking surface.

During a damping condition of the loads transferred on said main body 10 by the leg element, said plurality of partial contact conditions include at least a first contact position and a second contact position, preferably subsequent to each other, thereto a respective opposite motion of the actuation means 30 between the advanced position $P_{sup}$ and the backward position $P_{inf}$ corresponds.

Said first contact position may coincide, for example, with the step cycle beginning, when the heel terminal end H is the only region of the foot portion 11 in contact with the walking surface.

On the contrary, said second contact position may coincide with a terminal (sub)phase of the resting phase, when the user unbalances the load on the front portion of the foot portion 11, that is during the so-called "late stance".

Going back now to FIGS. 4A and 4B and assuming the above-mentioned second contact position wherein the user unbalances on the front on the foot portion 11, a clockwise torque $M_p$ is then generated causing a rotation of the supporting means 20 and then a rotation of the second arm BC around the joint G.

Said first arm DC is hinged at a first upper end C to said second arm BC at the nut screw element 32. At the opposite lower end D, the arm DC is hinged to an end of the static element DE.

Such configuration makes that the torque transmitted during the rotation of the second arm BC will result in a tension along the first arm DC with variable extension, that is along the axis of the screw element 31. Said tension is further transferred to the main body 10 through the static element DE.

Once known the tension performed along the first arm DC, the motor means 34 actuates a rotation of the screw element 31 corresponding to a roto-translation motion of the nut screw element 32 along the axis of the screw element 31.

The extension of the first arm DC is then increased since its hinged ends are at higher distance than the above-described initial resting condition. In particular, the roto-translation of the nut screw 32 corresponds to an advancing of the upper end C of the first arm DC towards the above-mentioned advanced position $P_{sup}$.

Such increases results in an increase of the internal angle $\alpha$ defined between the second arm BC and the static element AB and, then, in an actuation around the main rotation centre G of the ankle prosthesis 100.

Preferably said second arm BC has a length between 40 mm and 60 mm. Such size selection, provided in combination with the above-described four-bar linkage configuration 40, has the advantage of maximizing the useful space available for an anthropometric size of 50th percentile male ankle prosthesis even if by using a foot structure with energy return. Advantageously, even the wearability of the prosthesis 100 is consequently improved.

Analogously to what illustrated above and now by referring to the first contact position wherein the user unbalances the load on the heel terminal end H, the weight force mg will result to be applied on the left of the rotation centre B, at a distance for example d from the joint G, in this case by generating a counter-clockwise torque. Then, once the tension performed along the first arm DC (in this case compression tension) is known, the motor means 34 actuates the nut screw 32 in opposite direction with respect to the preceding example, by reducing the length of the first arm DC. Differently from the previous example, then, an actuation around the rotation centre B counter-clockwise will be obtained.

Advantageously, then, the damping can be generated in both moving directions of the actuator means 30, in order to obtain a damping in a first initial contact position, for example in plantarflexion (during the contact of the heel terminal end H) and, subsequently, a damping in a second contact position, for example in dorsiflexion (stance, late-stance).

The particular four-bar linkage configuration 40 and the implementation of the actuation means 30 as described above allows the prosthesis to be able to absorb energy in the resting phase (stance) and to actuate the joint during swinging (swing), by lifting the foot from the walking plane (toe clearance).

As mentioned above, differently from the known ankle prostheses wherein the motor means has the purpose of providing the torque necessary to annul the load transferred by the user in the stance phase, in the invention the actuation means 30 is configured to be able to dampen the load applied during the foot resting phase, through the actuation of the screw element 31 and the corresponding motion of the nut screw element 32.

Advantageously, the action of the actuation means 30 results to be proportional to the applied load, that is to the torques transmitted to the prosthesis 100 by the leg element during the various step phases, and it is "modulated" by the motor means 34 which can recognize the entity of the motion which the user is performing, or which he/she wants to perform, to provide the corresponding torque contribution.

Preferably, the prosthesis 100 of the invention comprises sensor means configured to actuate the actuation means 30 depending upon the detection of a variation in the tensional state, for example a flexion, of said main body 10. Through the sensor means for example it is possible to detect the torque due to the unbalance during a step beginning.

In a preferred embodiment, the sensor means comprises a control unit suitably configured to cooperate with Hall sensors. In the illustrated example, the control unit is assembled on the main body 10, preferably on the upright element 12, and it is equipped with magnetic elements 50 spaced apart therebetween and configured to cooperate with detection means 60.

In the illustrated example, an electronic group 80 is supported by the main body 10 with the purpose of controlling the motor means depending upon the data detected by the sensor means. The electronic group 80 can include micro-controller and power electronics. Preferably, the electronic group 80 is positioned below the supporting means 20 and fastened to the upright element 12.

When a torque is applied to the prosthesis 100, for example due to a rotation of the supporting means 20 around the joint G, the main body 10 bends and increases (or reduces) the distance between the magnetic elements 50 and the detection means 60. Such distance variation generates an intensity change in magnetic field detected by the detection means 60, which produces a voltage proportional to the detected flexion. By applying the mechanical formula related to the flexion of a beam it is possible to date back to the torque applied by the user' leg element to the ankle prosthesis 100.

The magnetic elements 50 can be distributed on the main body 10 so that the detection means 60 is capable of detecting how the distribution of the applied load transfers, for example, laterally inside or outside of the foot portion 11. In particular, in the illustrated embodiment and with reference to FIGS. 1 and 3, the upright element 12 comprises two side-by-side carbon blades, each one thereof has a magnet 50 facing a respective sensor 60 positioned frontally thereto at the electronic group 80. This functionality results to be very useful, especially during a calibration phase of the prosthesis 100, wherein the prosthetist can intervene in aligning the ankle once the feedback of the detection means 60 is given.

In general terms, the prosthesis 100 allows to adjust automatically its position during the swing phase (that is associated to the leg swinging) to engage the walking surface with the correct angulation, since it is capable of detecting early the user's intentions, by adapting automatically to the environment therewith it interacts.

The prosthesis 100 advantageously results to be configured for different use profiles. Such profiles can differ for example between normal walking, step climbing/descending and pace on diversified walking surfaces (cement, gravel, grass etc.).

Due to the conforming nature of the implementation, the prosthesis 100 of the invention allows the users to re-gain a more natural pace with respect, for example, to the passive ESAR foots, by reducing shocks and pain to the stump, usually associated to the use of classic prosthetic devices. Advantageously, the prosthesis 100 guarantees stability and allows to improve safety during walking by reducing the tripping hazards.

The use of the above-described actuation means 30 in combination with the four-bar linkage configuration 40 allows to reduce sizes and encumbrance of the motor means 34, then to reduce the overall dimensions of the prosthesis 100 and to increase the autonomy of the latter.

The precise selection of such architecture allows to obtain a transmission efficiency of the coupling between the screw element 31 and the nut screw element 32 comprised between 45% and 55%.

In general terms, as it is known, as the transmission efficiency increases, the efficiency of coupling between the screw element and the nut screw element increases and the coupling reversibility (backdriveability) is favoured and therefore a higher external contribution (breaking torque provided by the motor means) is required to prevent the nut screw element from roto-translating freely along the screw element.

In the invention case, an actuation of the nut screw element 32 by the motor means 34 "advancing" towards the advanced position $P_{sup}$ (in its own relative motion with respect to the screw element 31), favours lifting (toe clearance) of the foot portion 11 from the walking surface. At the same time, the nut screw element 32 results to be movable advancing towards the advanced position Psup during its own moving back (or retrograde motion) during the damping condition in the resting phase of the foot portion 11, in particular in the above-mentioned second contact position.

Therefore, the "moving back" difficulty of the nut screw element 32 on the screw element 31, in both directions along the damping direction S, allows damping in the resting phase (stance), that is sustaining the load transferred to the prosthesis 100 by the user's leg element.

Preferably, the coupling between the screw element 31 and the nut screw element 32 provides a breaking torque comprised between 80% and 120% of the load applied by the leg element to the prosthesis 100.

Advantageously, during the damping condition, the retrograde motion of the nut screw element 32 towards said rearward position $P_{inf}$ or towards said advanced position $P_{sup}$ can allow the regeneration of electric current during the resting phase with the purpose of making the prosthesis 100 rechargeable and energetically autonomous.

In other words, the four-bar linkage configuration 40 allows the actuation means 30 to act as damping element along the above-said damping direction S through the fine adjustment of reversibility parameters of said coupling. Said reversibility parameters comprise the friction coefficient of the coupling between screw element 31 and nut screw element 32 and, preferably, the helix angle of the screw element 31.

In a preferred sizing of the invention, said reversibility parameters provide a transmission efficiency of the coupling equal to 50%.

Preferably, for a friction coefficient value equal to 0.16 between the screw element 31 and the nut screw element 32, the screw element has a helix angle comprised between 3° and 11°.

The above-mentioned friction coefficient is preferably obtained starting from selected treatments of the screw-nut screw coupling, for example through a diamond like carbon (DLC) coating applied to the screw element 31. In this way the system efficiency is improved without sacrificing a high transmission ratio. Analogous treatments, advantageously, allow to make the nut screw element 32 of steel instead of bronze (as known in the couplings of this type) by increasing the component yield strength and thus implementing a more compact mechanism. Some examples are polytetrafluoroethylene (PTFE) treatments, tungsten disulphide ($WS_2$) and molybdenum disulphide ($MoS_2$) treatments.

The helix angle of the screw element 31 was selected specifically to determine the wished coupling efficiency and to reduce to the minimum the sizes and the consumption of the motor means 34 according to the proportional brake principle as described above.

According to a preferred embodiment, the screw element 31 is made of steel e the nut screw element 32 is made of a material comprising steel, bronze, brass or a reinforced polymer.

In particular, given a helix angle θ of the screw element 31, this is preferably linked to the real step L of the screw element 31 and to the primitive diameter of the screw element 31 according to formula:

$$\theta = \arctan\left(\frac{L}{\pi D}\right)$$

Moreover, said helix angle θ is preferably calculated depending upon the friction coefficient μ according to formula:

$$\theta = \tan^{-1}\left(\frac{1}{4\mu} - \sqrt{\frac{1}{16\mu^2} - \frac{1}{2}}\right)$$

wherein μ is the dynamic friction coefficient between the screw element 31 and the nut screw element 32.

The present invention has been sofar described with reference to preferred embodiments thereof. It is to be meant that each one of the technical solutions implemented in the preferred embodiments, herein described by way of example, could advantageously be combined differently therebetween, to create other embodiments, belonging to the same inventive core and however all within the protective scope of the here-below reported claims.

The invention claimed is:

1. An ankle prosthesis comprising:

a main body, having a foot portion configured to rest on a walking surface;

stump supporting means, configured to couple with a leg prosthetic element;

linear actuation means, comprising a coupling between a screw element and a nut screw element having a friction coefficient lower than 0.16, wherein said stump supporting means, said screw element and said nut screw element are constrained to said main body according to a substantially four-bar linkage configuration, so that a relative rotation between said supporting means and said main body is allowed and so that said actuation means is configured to act as damping element along a damping direction (S) and is movable between an advanced position ($P_{sup}$) and a rearward position ($P_{inf}$) with respect to said damping direction (S), wherein said foot portion comprises a first and a second contact position during a resting phase on the walking surface, wherein to said first and second contact position corresponds a respective opposite movement of said actuation means between said advanced position ($P_{sup}$) and said rearward position ($P_{inf}$) during a damping condition of the loads transferred on said main body by the leg element.

2. The ankle prosthesis according to claim 1, wherein said actuation means is movable in approach to said rearward position ($P_{inf}$) in said first contact position and is movable in approach to said advanced position ($P_{sup}$) in said second contact position.

3. The ankle prosthesis according to claim 1, wherein said damping direction (S) is parallel to the axis of said screw element.

4. The ankle prosthesis according to claim 1, wherein the efficiency of the coupling between said screw element and said nut screw element is between 45% and 55%.

5. The ankle prosthesis according to claim 1, wherein said screw element has a helix angle of between 3° and 11°.

6. The ankle prosthesis according to claim 1, wherein said screw element is treated with a treatment selected from the group consisting of a diamond like carbon (DLC) treatment, a polytetrafluoroethylene treatment, a tungsten disulfide treatment and a molybdenum disulfide treatment.

7. The ankle prosthesis according to claim 1, wherein said screw element is made of steel and said nut screw element is made of a material selected from the group consisting of steel, bronze, brass and a reinforced polymer.

8. The ankle prosthesis according to claim 1, wherein a first arm of said four-bar linkage has a variable extension according to the rotation of said supporting element, said extension being variable between said advanced position ($P_{sup}$) and said rearward position ($P_{inf}$).

9. The ankle prosthesis according to claim 1, wherein a second arm of said four-bar linkage connects said supporting element and said nut screw element to each other.

10. The ankle prosthesis according to claim 9, wherein said second arm has a length between 40 mm and 60 mm.

11. The ankle prosthesis according to claim 1, wherein said supporting element and said main body are coupled at a joint lying on an axis, wherein said axis orthogonally intercepts a direction of development of said foot portion, when resting on the walking surface, at one third of its extension with respect to a heel terminal end.

12. The ankle prosthesis according to claim 1, wherein said actuation means comprises a planetary reduction gear.

13. The ankle prosthesis according to claim 1, further comprising sensor means configured to actuate said actuation means in function of a detection of a bending of said main body.

14. The ankle prosthesis according to claim 1, wherein said main body comprises an energy-returning carbon fibre foot structure.

* * * * *